United States Patent
Fan

(10) Patent No.: US 9,427,225 B2
(45) Date of Patent: Aug. 30, 2016

(54) TISSUE LIFTING

(75) Inventor: Wei Li Fan, Boston, MA (US)

(73) Assignee: Smith & Nephew, Inc., Memphis, TN (US)

(*) Notice: Subject to any disclaimer, the term of this patent is extended or adjusted under 35 U.S.C. 154(b) by 174 days.

(21) Appl. No.: 14/007,434

(22) PCT Filed: Mar. 23, 2012

(86) PCT No.: PCT/US2012/030399
§ 371 (c)(1),
(2), (4) Date: Jan. 24, 2014

(87) PCT Pub. No.: WO2012/135045
PCT Pub. Date: Oct. 4, 2012

(65) Prior Publication Data
US 2014/0187869 A1    Jul. 3, 2014

Related U.S. Application Data

(60) Provisional application No. 61/467,413, filed on Mar. 25, 2011.

(51) Int. Cl.
*A61B 17/02* (2006.01)
*A61B 17/04* (2006.01)

(52) U.S. Cl.
CPC ......... *A61B 17/025* (2013.01); *A61B 17/0401* (2013.01); *A61B 2017/0409* (2013.01); *A61B 2017/0414* (2013.01); *A61B 2017/0441* (2013.01); *A61B 2017/0448* (2013.01); *A61B 2017/0464* (2013.01)

(58) Field of Classification Search
CPC .... A61B 17/02; A61B 17/04; A61B 17/025; A61B 17/0401
USPC .................................................. 600/201–246
See application file for complete search history.

(56) References Cited

U.S. PATENT DOCUMENTS

| | | | | |
|---|---|---|---|---|
| 5,582,616 A | * | 12/1996 | Bolduc | A61B 17/064 606/139 |
| 5,626,613 A | * | 5/1997 | Schmieding | A61B 17/0401 24/711.3 |
| 6,663,633 B1 | * | 12/2003 | Pierson, III | A61B 17/0469 606/148 |
| 2004/0193217 A1 | | 9/2004 | Lubbers et al. | |
| 2007/0118151 A1 | | 5/2007 | Davidson | |
| 2008/0288060 A1 | | 11/2008 | Kaye et al. | |
| 2009/0112214 A1 | * | 4/2009 | Philippon | A61B 17/025 606/90 |
| 2009/0276038 A1 | * | 11/2009 | Tremulis | A61B 17/0401 623/2.11 |
| 2010/0161042 A1 | | 6/2010 | Maisano et al. | |
| 2011/0118757 A1 | * | 5/2011 | Pierce | A61B 17/0482 606/144 |

FOREIGN PATENT DOCUMENTS

| | | |
|---|---|---|
| EP | 1 759 663 | 3/2007 |
| EP | 1759663 A2 | 3/2007 |
| WO | 2005/102181 | 11/2005 |
| WO | 2005/102181 A1 | 11/2005 |

* cited by examiner

*Primary Examiner* — Christopher Beccia
(74) *Attorney, Agent, or Firm* — Burns & Levinson LLP; Joseph M. Maraia

(57) ABSTRACT

A device (100) includes a shaft (108), a coil (120), and a suture (106). The coil has a sharp tip (126) and is releasably coupled to the shaft. The suture is coupled to the coil and extends through the shaft.

23 Claims, 6 Drawing Sheets

TISSUE LIFTING

RELATED APPLICATIONS

This application is the U.S. National Stage of International Application No. PCT/US12/30399, filed on Mar. 23, 2012, which claims priority to and the full benefit of U.S. Provisional Application Ser. No. 61/467,413, filed Mar. 25, 2011, the entire contents of which are incorporated herein by reference.

CROSS-REFERENCE TO RELATED APPLICATION

This application claims priority to and the full benefit of U.S. Provisional Application Ser. No. 61/467,413, filed Mar. 25, 2011, and titled "Device for Use In Hip Arthroscopy," the entire contents of which are incorporated herein by reference.

TECHNICAL FIELD

This application relates to surgical devices.

BACKGROUND

Generally, tissue distractors are used for expanding or separating tissues in order to create a space between the tissue to improve visualization and for increased working space during open surgery and minimally invasive surgery.

For example, during arthroscopic surgery, the joint areas of the body, such as the hip, knee, shoulder, and other joint areas, are approached via the use of an endoscope. Some joints are harder to access than others. For example, the hip joint differs from other joints in that a thick layer of soft tissue, known as the hip capsule, surrounds it. This thick layer makes changing the trajectory of instruments placed into the joint difficult and the importance of placing portals, or tissue passages, more critical than other joints.

During such surgeries, it is important to minimize the amount and size of incisions in order to reduce healing times. Conventional retractors are often bulky and awkward and require substantially large open incisions in a skin surface which may damage large amounts of healthy tissue.

Accordingly, there exists a need for a surgical device that may be modified to assist in cannula access to various treatment sites within a patient body for surgery.

SUMMARY

In a general aspect, a device includes a shaft, a coil, and a suture. The coil has a sharp tip and is releasably coupled to the shaft. The suture is coupled to the coil and extends through the shaft.

Implementations may include one or more of the following features. For example, the device may also include a handle coupled to the shaft which defines a passageway through the handle. The shaft may define a longitudinal passageway that cooperates with the passageway defined through the handle to receive the suture. The shaft may be rigid. The device may also include an interface that is releasably coupled to one of the coil and the shaft. The interface may define an opening that is receives a mating portion of the shaft. The interface and the shaft, when coupled, may permit the sharp tip of the coil to be driven into tissue upon rotation of the coupled interface and shaft. The interface may include an element for releasably securing the suture to the coil. The interface may be releasably coupled to the coil.

In another general aspect, a method of lifting tissue includes advancing a coil into the tissue, the coil having a suture attached thereto, and tensioning the suture to lift the tissue.

Implementations may include one of more of the following features. For example, tensioning the suture may include pulling on a proximal end of the suture with sufficient force to lift the tissue. Advancing the coil may include rotating a driver releasably coupled to the coil. The method may also include retracting the driver, leaving the coil in the tissue. The driver may be releasably coupled to the coil by engaging a distal end of the driver with a mating surface formed in an interface coupled to the coil. The tissue may comprise a hip capsule. The driver may have a rigid shaft.

It should be understood that the drawings are not necessarily to scale and that the disclosed implementations are sometimes illustrated diagrammatically and in partial views. In certain instances, details which are not necessary for an understanding of the disclosure or which render other details difficult to perceive may have been omitted. It should be understood, of course, that this disclosure is not limited to the particular implementations illustrated herein.

DETAILED DESCRIPTION

Figure 1:
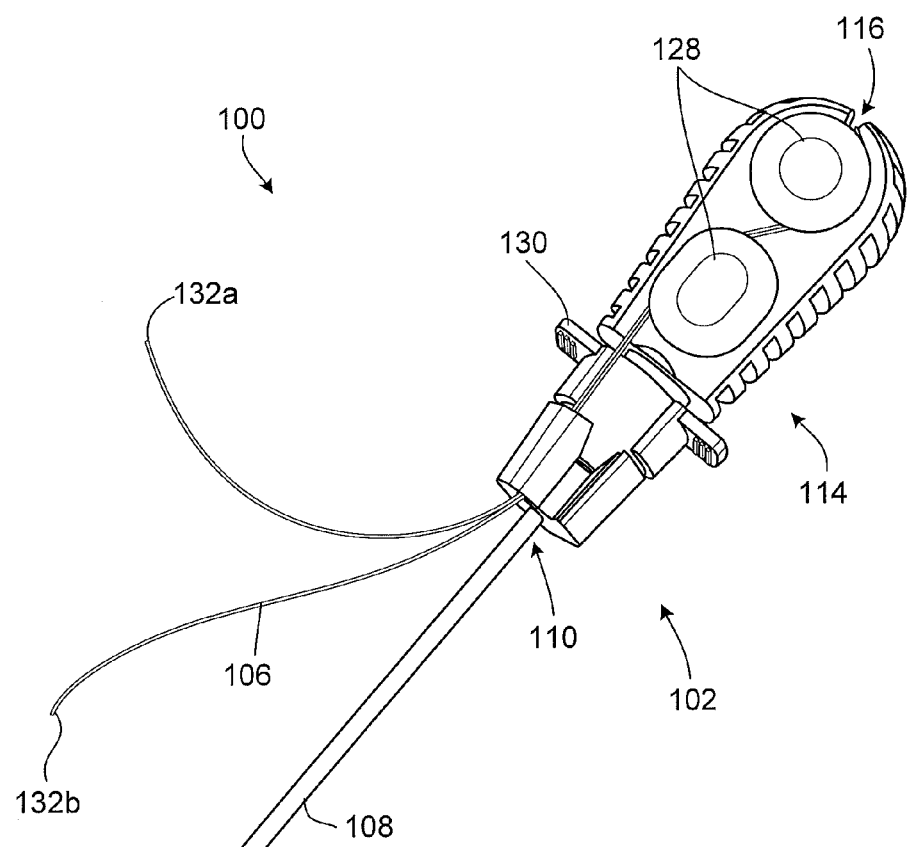
FIG. 1 is a perspective view of a tissue lift assembly.
Figure 1:
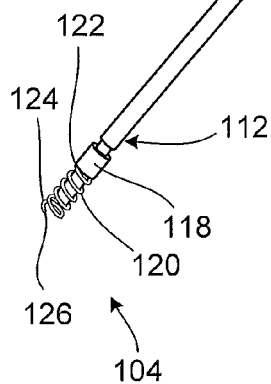
Figure 2:
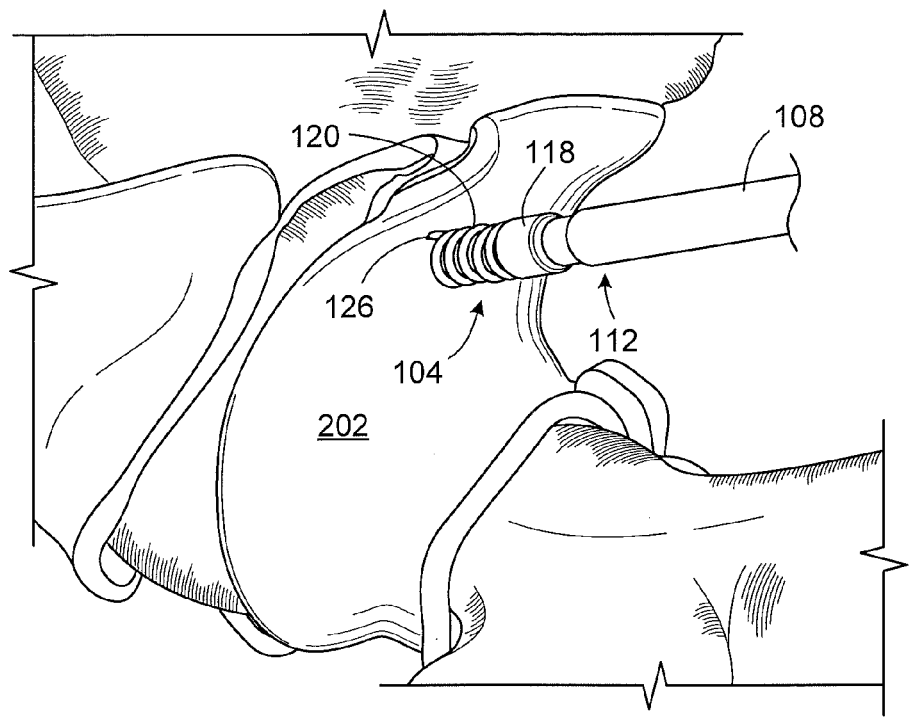
FIGS. 2-9 illustrate a method of using a tissue lift assembly.
Figure 3:
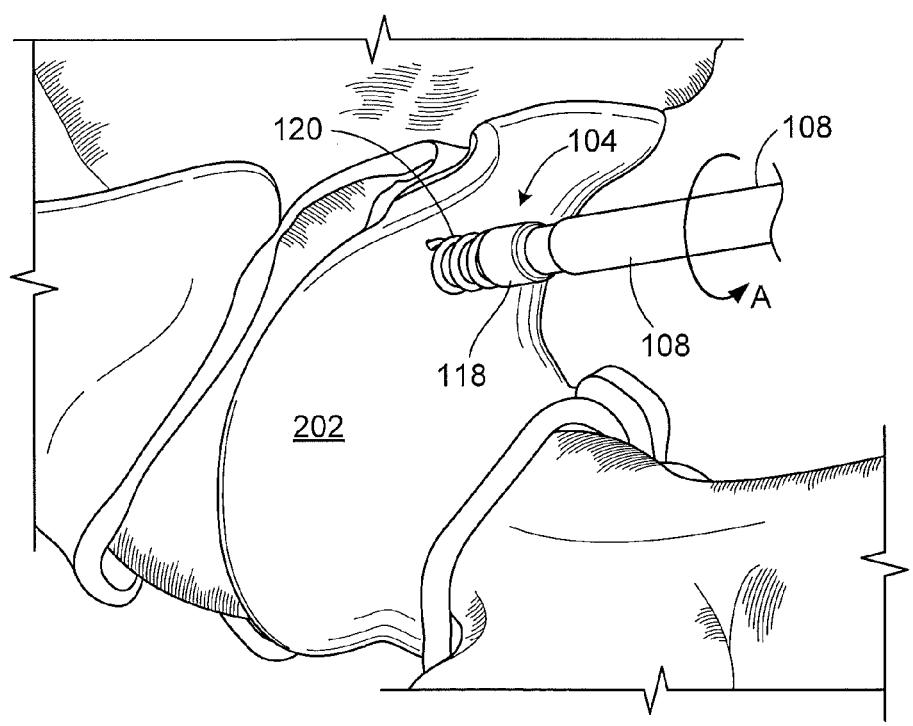
Figure 4:
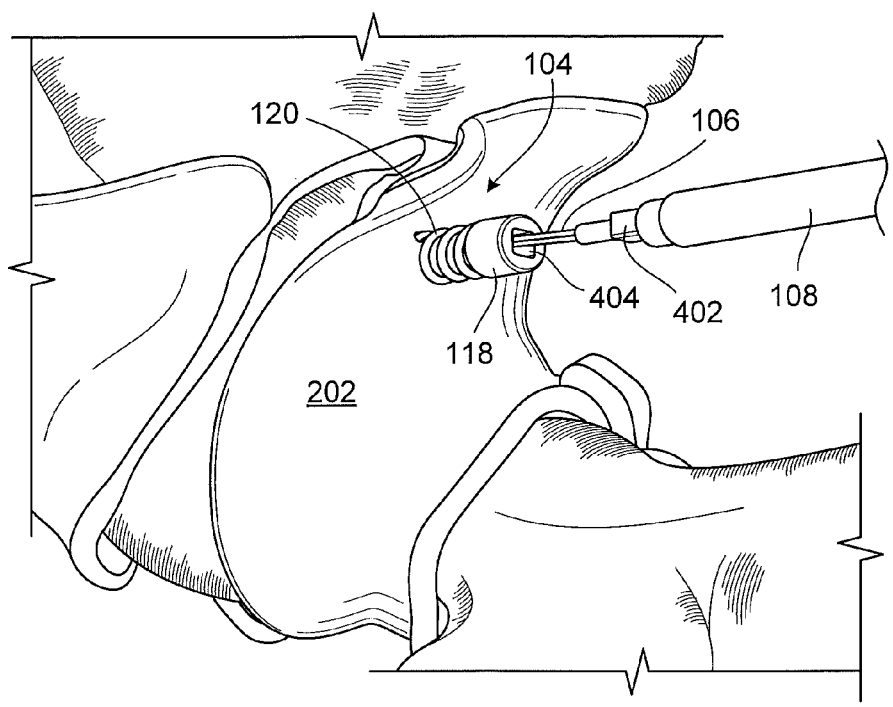
Figure 5:
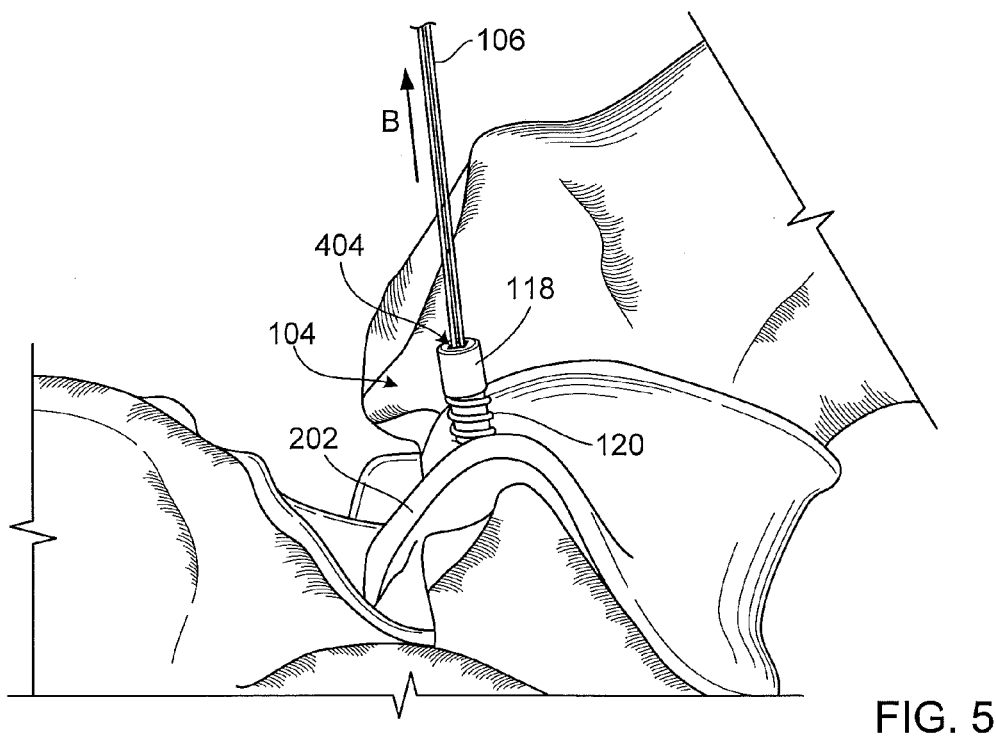
Figure 6:
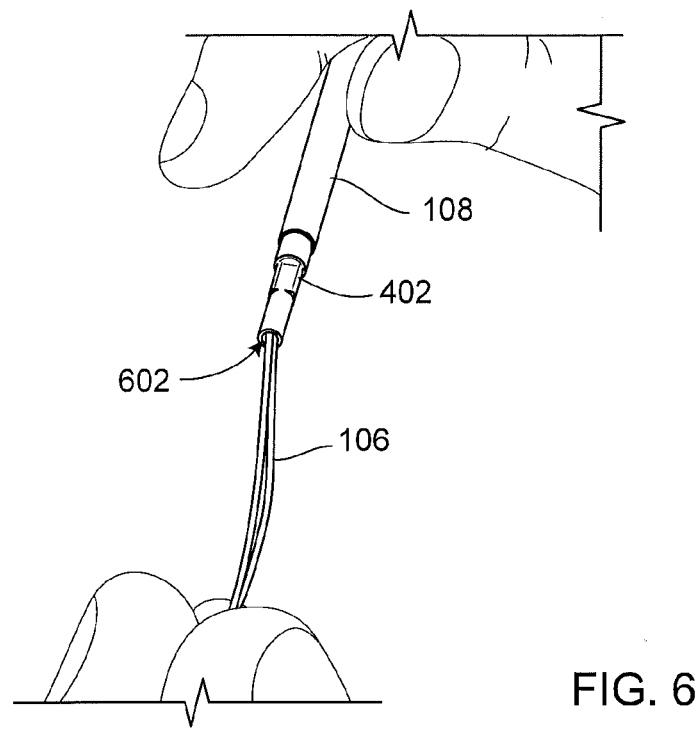
Figure 7:
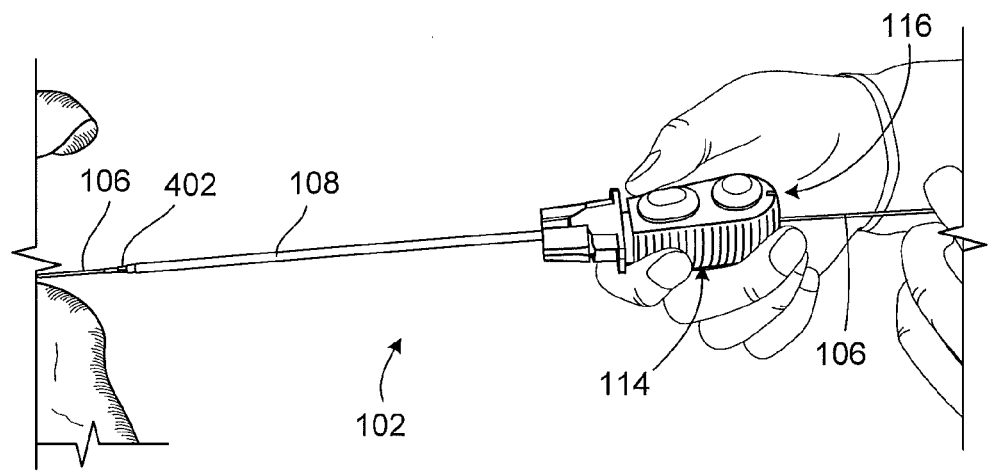

FIG. 1 shows a tissue lift assembly 100. The tissue lift assembly 100 includes a driver 102, an inserter 104, a coil 120, and a flexible member, such as a suture 106. The driver 102 includes a shaft 108 with a proximal end 110 and a distal end 112. A handle 114 is coupled to the proximal end 110 of the shaft, and the distal end 112 of the shaft 108 includes a mating portion 402 (FIG. 4). The shaft 108 may define a channel or lumen 602 (FIG. 6) extending from the proximal end 110 and the distal end 112. The handle 114 may include suture retention features such as protuberances 128 and switch 130. The switch 130 may be spring loaded. The handle 114 defines a longitudinal passageway 116 extending through the handle 114 that may align with the channel or lumen 602 of the shaft 108 when, for example, the shaft 108 is coupled to the handle 114.

The inserter 104 includes an interface portion 118 that may be releasably coupled to the coil 120 and that defines an opening or recess 404 (FIG. 4). The opening 404 in the interface portion 118 is shaped and configured to receive the corresponding mating portion 402 of the shaft 108.

The coil 120 is coupled to the interface portion 118 at its proximal end 122. The distal end 124 of the coil 120 forms a sharp tip 126. A distal end portion (not shown) of the suture 106 is releasably or permanently coupled to the coil 120 or interface portion 118 and extends through the lumen 602 (FIG. 6) of the shaft 108 and through the passageway 116 of the handle 114. Proximal end portions 132a and 132b of the suture 106 extend from the passage way 116 of the handle 114 and may be engaged with the suture retention features 128 and 130. In particular, the end portions 132a and 132b may be threaded through and around retention features 128 on a side of the handle 114 and through a retention notch (not shown) formed in the switch 130.

To assemble the tissue lift assembly 100, the inserter 104 is brought into contact with the distal end 112 of the shaft 108 by tensioning the suture 106. Tension may be maintained on the suture 106 with the use of suture retention features 128 and 130 or manually.

Referring to FIGS. 2-9, in use, access portals (not shown) are created in, for example, tissue surrounding the hip. These portals allow surgeons to access the desired surgery location with minimal damage to surrounding tissue. Often it is necessary to lift tissue away from a bone, joint, or wound in order to access the desired surgery location. FIGS. 2-9 illustrate the use of the tissue lift assembly 100 to lift a hip capsule 202 away from the hip joint. The tissue lift assembly 100 is assembled as shown in FIG. 1 by bringing the inserter 104 into contact with the distal end 112 of the shaft 108 by pulling on the end portions 132a and 132b of suture 106. In the implementation shown, the coil 120 and the interface 118, which are releasably coupled to the distal end 112 of the shaft 108, are then inserted through a portal (not shown) in the patient's skin and other tissue. The driver 102 is used to bring the sharp tip 126 of the coil 120 into contact with tissue, such as the hip capsule 202. The shaft 108 is then rotated in a counterclockwise direction as indicated by arrow A (FIG. 3), by rotating the handle 114. This rotation causes the sharp tip 126 to pierce the tissue 202 and drives the coil 120 into tissue 202. Referring to FIG. 4, once the coil 120 is inserted in the tissue 202 at the desired depth, the mating portion 402 of the shaft 108 may be released from the opening 404 of the interface 118 by, for example, releasing the suture 106 from the suture retention features 128 and 130 (FIG. 1) and pulling the driver 102 away from the inserter 104. The shaft 108 can then be removed completely from the portal (not shown) leaving the coil 120, the interface 118, and a portion of the suture 106 within the surgical site. Removing the shaft 108 from the portal conserves space in the portal by leaving only the thin suture 106, allowing for insertion of another device through the same portal while the inserter 104 is being used. To lift the tissue 202, tension is applied to the suture 106 as illustrated by arrow B (FIG. 5), with sufficient force to lift the tissue to a desired distance from the bone, joint, or wound area.

Figure 8:
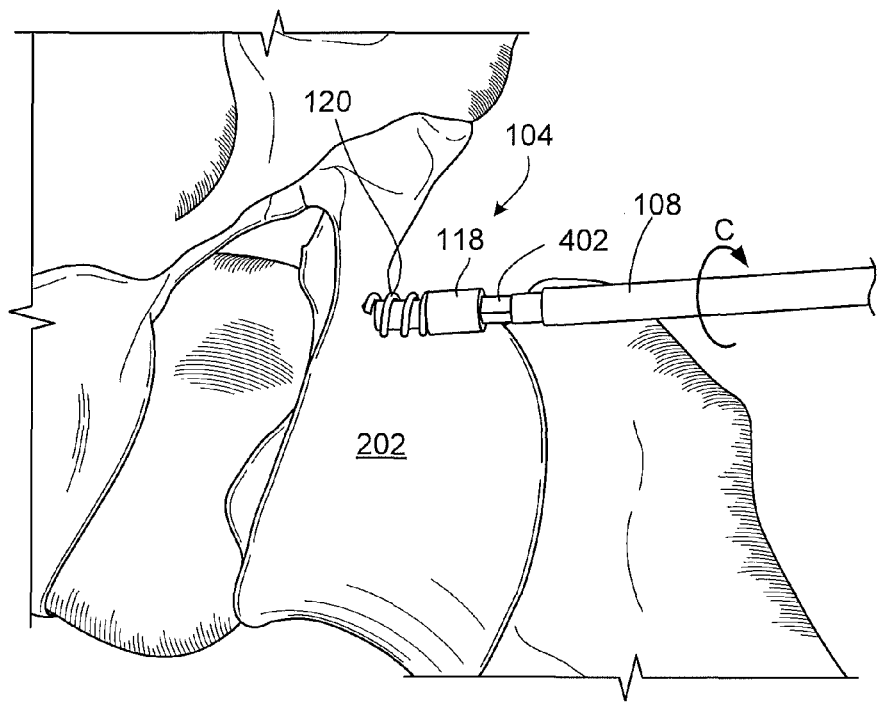
Figure 9:
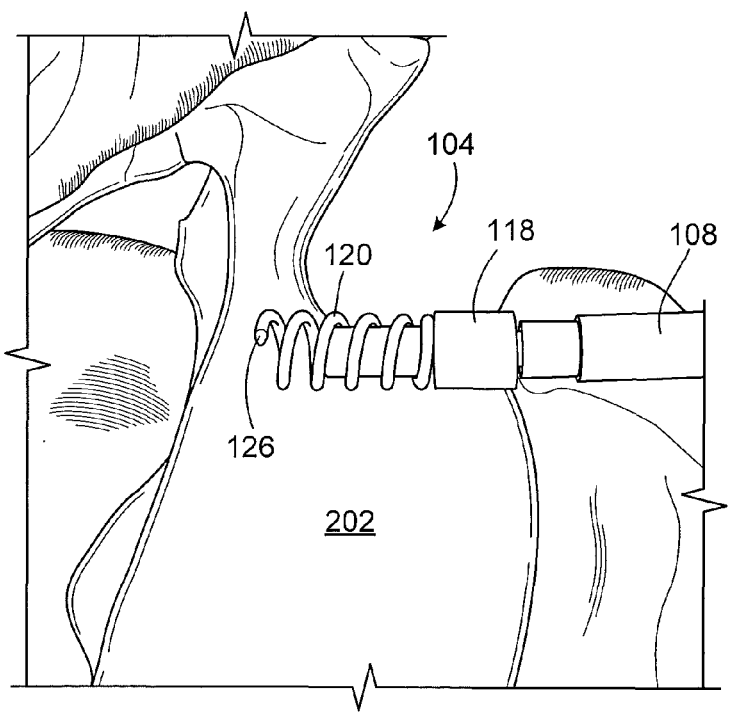

To remove the coil 120 from the tissue 202, while holding the end portions of the suture 106, the shaft 108 of the driver 102 is slid proximally along the suture 106 until the mating tip 402 on the distal end 112 of the shaft 108 contacts with the opening 404 of the interface 118 (FIG. 8). The surgeon may then engage the suture 106 with the suture retention features 128 and 130 to maintain the contact between the shaft 108 and the coil 120, and more specifically, the interface 118 with the mating tip 402 of the shaft 108. The shaft 108 may then be rotated in a clockwise direction as indicated by arrow C (FIG. 8), by rotating the handle 114 in a clockwise direction. This rotation causes the coil 120 to be drawn from the tissue 202. Once the sharp tip 126 of the coil 120 is free of the tissue 202, the entire tissue lift assembly 100 may be removed from the portal (not shown).

Figure 10:
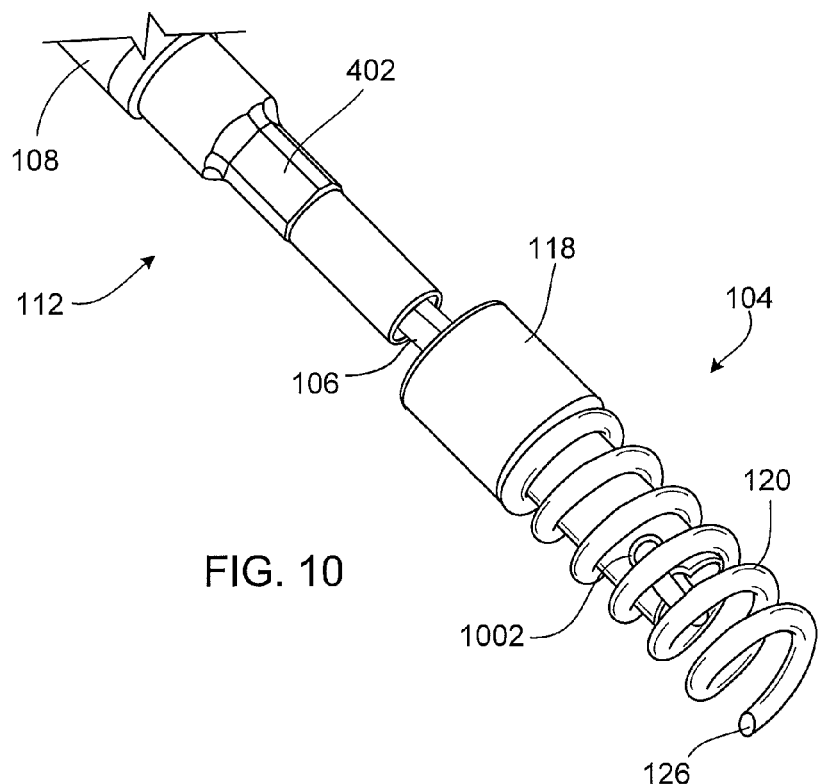
FIG. 10 is a perspective view of a distal portion of a tissue lift assembly.
Figure 11:
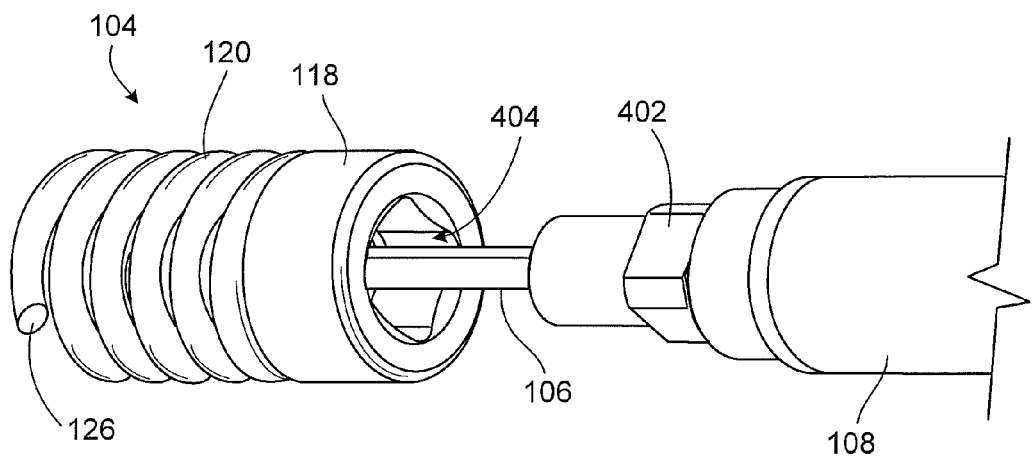
FIG. 11 is a side plan view of a distal portion of a tissue lift assembly.

FIGS. 10 and 11 show an exploded view of the distal end of the tissue lift assembly 100. The distal end 112 of the shaft 108 includes a mating portion 402 that is shaped as a square driver. The interface 118 may be coupled to the coil 120 and defines an opening 404, which is shaped to receive the mating portion 402 of the shaft. A suture 106 extends from the shaft 108 and into interface 118. Interface 118 includes slots or other retention features 1002 to releasably couple the suture 106 to the interface 118 and the coil 120.

While only certain implementations have been set forth, alternatives and modifications will be apparent from the above description to those skilled in the art. For example, the suture 106 may be coupled to the interface 118 or may be releasably and directly coupled to the coil 120. In addition, the present implementations also are not limited to sutures, but may include other flexible members. The shaft 108 may be rigid or flexible.

In addition, the coil 120 is not limited to the spring-like coil illustrated, but may include other types of coils such as threads around a tapered cylinder, spiral cannulas, etc. The cross section of the coil 120 may be triangular, polygonal, or any other shape. Likewise, the coil 120 may be designed to be inserted by rotating clockwise and removed by rotating counterclockwise or by moving the coil in a different manner, such as in a substantially linear motion.

The coil 120 and the interface 118 may be releasably or directly coupled. The mating portion 402 and the opening 404 to receive the mating portion 402 may be shaped differently. Likewise, the interface 118 may include a mating portion while the shaft 108 includes an opening to receive the mating portion.

These and other alternatives are considered equivalents and within the spirit and scope of this disclosure and the appended claims.

The invention claimed is:

1. A method for lifting tissue, comprising:
    advancing a tissue lifting member into the tissue, via an insertion instrument, the tissue lifting member having a suture attached thereto;
    wherein a driver is releasably coupled to the tissue lifting member by engaging a distal end of the driver with a mating surface formed in an interface coupled to the tissue lifting member;
    disengaging the tissue lifting member from the insertion instrument; and
    tensioning the suture, after disengaging the tissue lifting member, to lift the tissue away from a surgical site in order to access the surgery site.

2. The method of claim 1, wherein tensioning the suture comprises pulling on a proximal end of the suture with sufficient force to lift the tissue.

3. The method of claim 1, wherein advancing the tissue lifting member comprises rotating the driver releasably coupled to the tissue lifting member.

4. The method of claim 3, further comprising retracting the driver leaving the tissue lifting member in the tissue.

5. The method of claim 1, wherein the tissue comprises a hip capsule.

6. The method of claim 3, wherein the driver has a rigid shaft.

7. A tissue lifting assembly, comprising:
    a shaft;
    a tissue lifting member releasably coupled to the shaft via an interface portion; and
    a suture coupled to the tissue lifting member, the suture extending through the shaft,
    wherein the interface portion is coupled to the tissue lifting member and wherein one of (i) the interface portion defines a central opening or recess configured to receive a corresponding mating portion of the shaft or (ii) the shaft defines a central opening or recess configured to receive a corresponding a mating portion of the interface portion.

8. The tissue lifting assembly of claim 7, wherein the tissue lifting member includes a series of loops, in use, the series of loops being inserted into tissue.

9. The tissue lifting assembly of claim 8, wherein the series of loops forms a helical coil.

10. The tissue lifting assembly of claim 8, wherein the series of loops forms threads around a tapered cylinder.

11. The tissue lifting assembly of claim 8, wherein the series of loops forms a spiral cannula.

12. The tissue lifting assembly of claim 8, wherein the series of loops is adapted to being rotated into tissue.

13. The tissue lifting assembly of claim 8, wherein the series of loops is adapted to being moved into tissue, linearly.

14. The tissue lifting assembly of claim 8, wherein the series of loops has a triangular or polygonal cross section.

15. The tissue lifting assembly of claim 7, wherein the shaft is rigid.

16. The tissue lifting assembly of claim 7, further comprising a sharp tip at a distal end of the tissue lifting member.

17. The tissue lifting assembly of claim 7, further comprising a handle coupled to the shaft and defining a passageway through the handle.

18. The tissue lifting assembly of claim 17, wherein the shaft defines a longitudinal passageway therethrough that cooperates with the passageway defined through the handle to receive the suture therethrough.

19. The tissue lifting assembly of claim 7, wherein the interface portion and the shaft, when coupled, permit the tissue lifting member to be driven into tissue upon rotation of the coupled interface and shaft.

20. The tissue lifting member of claim 7, wherein the interface portion comprises an element for releasably securing the suture to the interface portion thereby releasably securing the suture to the tissue lifting member.

21. The tissue lifting assembly of claim 7, wherein the interface portion is releasably coupled to the tissue lifting member.

22. The tissue lifting assembly of claim 7, wherein the interface portion defines a central opening or recess configured to receive a corresponding mating portion of the shaft and wherein the suture extends through the central opening or recess in the interface portion prior to extending through the shaft.

23. The tissue lifting assembly of claim 7, wherein the suture is coupled relative to the tissue lifting member with respect to an anchor point along a central axis thereof.

* * * * *